United States Patent

Boyd et al.

[11] Patent Number: 5,750,720
[45] Date of Patent: *May 12, 1998

[54] 4-[(THIEN-3-YL)METHYL]-IMIDAZOLE ANALGESICS

[75] Inventors: Robert E. Boyd, Horsham; Chris Royce Rasmussen, Lansdale, both of Pa.; Jeffrey B. Press, Brewster, N.Y.

[73] Assignee: Ortho Pharmaceutical Corporation, Raritan, N.J.

[*] Notice: The term of this patent shall not extend beyond the expiration date of Pat. No. 5,621,113.

[21] Appl. No.: 625,442

[22] Filed: Mar. 28, 1996

[51] Int. Cl.$^6$ .................................................. C07D 411/06
[52] U.S. Cl. .................................................. 548/315.1
[58] Field of Search .................................................. 548/315.1

[56] References Cited

U.S. PATENT DOCUMENTS 5,621,113  4/1997  Boyd et al. .................... 548/315.1

FOREIGN PATENT DOCUMENTS 1-242571  9/1989  Japan.

OTHER PUBLICATIONS

Kihara et al., CA 112:139033, 1990.

*Primary Examiner*—Johann Richter
*Assistant Examiner*—Laura L. Stockton

[57] ABSTRACT

Described herein are 4-[(thien-3-yl)methyl]-imidazoles of the formula:

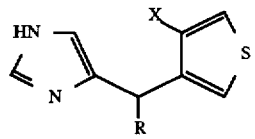

wherein

R is hydrogen or methyl, and

X is $C_{1-4}$alkyl, bromine or chlorine; or

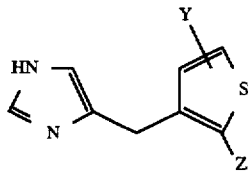

wherein

Y is hydrogen, $C_{1-4}$alkyl, bromine or chlorine, and

Z is $C_{1-4}$alkyl, bromine or chlorine which have exceptional analgesic activity.

4 Claims, No Drawings

4-[(THIEN-3-YL)METHYL]-IMIDAZOLE ANALGESICS

The present invention relates to $\alpha_2$-adrenoceptor agonists having analgesic activity. More particularly, the present invention relates to 4-[(thien-3-yl)methyl]-imidazoles having improved analgesic activity.

BACKGROUND OF THE INVENTION

Clonidine is a centrally acting $\alpha_2$-adrenoceptor agonist with wide clinical utility as an antihypertensive agent. Clonidine is believed to act by inhibiting the release of norepinephrine from sympathetic nerve terminals via a negative feedback mechanism involving $\alpha_2$-adrenoceptors located on the presynaptic nerve terminal. This action is believed to occur in both the central (CNS) and peripheral (PNS) nervous systems. More recently, the role of $\alpha_2$-adrenoceptor agonists as analgesic agents in humans and antinociceptive agents in animals has been demonstrated. Clonidine and other $\alpha_2$-adrenoceptor agonists have been shown to produce analgesia through a non-opiate mechanism and, thus, without opiate liability. However, other behavioral and physiological effects were also produced, including sedation and cardiovascular effects.

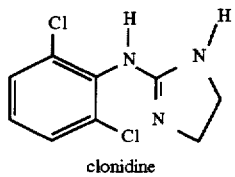

clonidine

Medetomidine and detomidine are $\alpha_2$-adrenoceptor agonists widely used clinically in veterinary medicine as sedatives/hypnotics for pre-anaesthesia. These compounds are hypotensive in animals and in humans, but the magnitude of this cardiovascular effect is relatively insignificant.

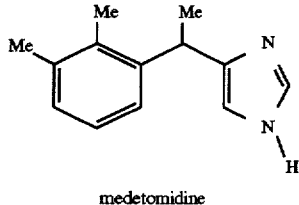

medetomidine

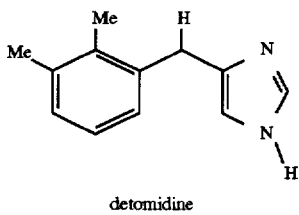

detomidine

U.S. Pat. No. 3,574,844, Gardocki et al., teach 4-[4(or 5)-imidazolylmethyl]-oxazoles as effective analgesics. The disclosed compounds are of the general formula:

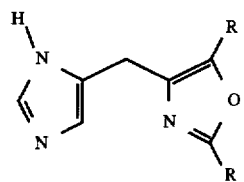

Compounds of this type are insufficiently active and suffer from unwanted side effects.

U.S. Pat. No. 4,913,207, Nagel et al., teach arylthiazolylimidazoles as effective analgesics. The disclosed compounds are of the general formula:

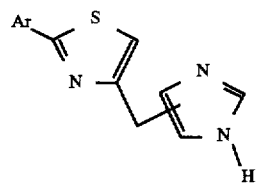

Compounds of this type are insufficiently active and suffer from unwanted side effects.

WO92/14453, Campbell et al., teach 4-[(aryl or heteroaryl)methyl]imidazoles as effective analgesics. The disclosed compounds are of the general formula:

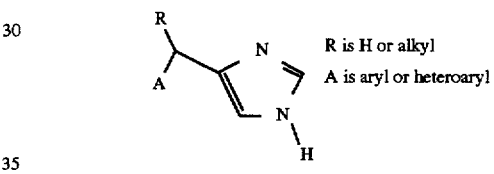

R is H or alkyl
A is aryl or heteroaryl

The disclosed compounds are insufficiently active and suffer from unwanted side effects.

Kokai No. 1-242571, Kihara et al., disclose a method to produce imidazole derivatives for use, among other uses, as antihypertensive agents.

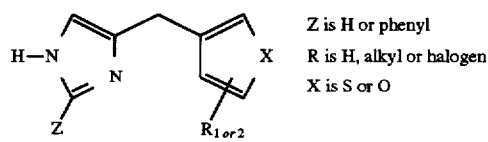

Z is H or phenyl
R is H, alkyl or halogen
X is S or O

A single mixture of compounds meeting the above formula was reportedly produced by the inventive method. This was a mixture of 4-(2-thienyl)-methylimidazole and 4-(3-thienyl)-methylimidazole represented by the following formula:

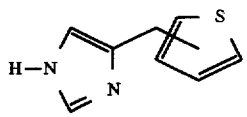

The disclosed compounds are insufficiently active and suffer from unwanted side effects.

It is an object of the present invention to produce 4-[(thien-3-yl)methyl]-imidazoles having improved analgesic activity.

It is another object of the present invention to produce 4-[(thien-3-yl)methyl]-imidazole analgesics having reduced side effects.

SUMMARY OF THE INVENTION

Briefly, there is provided by the present invention compounds having improved analgesic activity of the formulae:

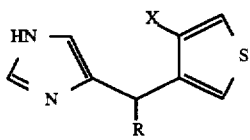

wherein

R is hydrogen or methyl, and
X is $C_{1-4}$alkyl, bromine or chlorine; or

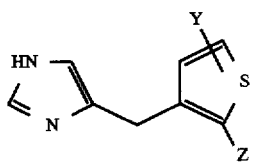

wherein

Y is hydrogen, $C_{1-4}$alkyl, bromine or chlorine, and
Z is $C_{1-4}$alkyl, bromine or chlorine.

DETAILED DESCRIPTION OF THE INVENTION

The compounds of the present invention may be made in basically a two step process. In the first step, an appropriately substituted precursor thiophene is obtained having hydrogen, $C_{1-4}$alkyl, bromine or chlorine substituents as desired and in the required positions. This precursor thiophene will have an electrophilic carbon substituent at the 3-position. In the second step, a precursor imidazole having an anion at the 4-position capable of reacting with the electrophilic carbon of the precursor thiophene to leave a carbon bridge residue, is reacted with the precursor thiophene to produce the target skeleton followed by deoxygenation of the carbon bridge residue. Of course, many variations are possible. It may be desirable to substitute the thiophene initially, as described, or to modify the substitution on the thiophene following the formation of the base structure of the final compound. Also, in compounds where it is desirable to have methyl substitution on the carbon bridge residue, additional steps will be necessary.

Herein, a Grignard reaction is favored for use in the second step to join the thienyl moiety and the imidazolyl moiety. Thus, it is preferred that the precursor imidazole be substituted at the 4-position as a Grignard reagent and that the precursor thiophene is substituted at the 3-position with a carbonyl, such as, formyl or N,O-dimethylcarboxamido group.

The preferred precursor imidazole has the formula:

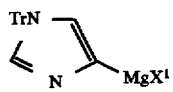

where $X^1$ is iodo, bromo or chloro. This compound may be made by methods well known to the art, i.e., reaction between alkyl Grignard or magnesium and imidazolyl halide in dry, alcohol-free ether or THF or dichloromethane.

The preferred precursor thiophenes have the formula:

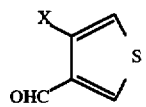

or

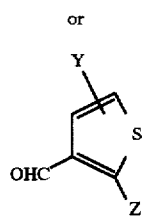

or

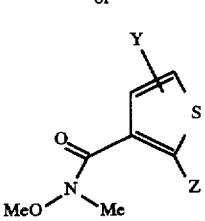

where X, Y and Z are defined above. As starting materials to make the preferred precursor thiophenes AA, BB and CC, the preparation of various brominated and methylated thiophenes is well known from the literature.

Precursor thiophenes of type AA may be produced from 3-bromo-4-methylthiophene or 3-bromo-4-(bromo or chloro)thiophene by use of halogen metal exchange. In a first step, the compound is treated with an organo-alkali compound such as n-butyllithium, the product of which is reacted, in a second step, in situ with DMF. The reaction is quenched with aqueous ammonium chloride. The resultant compound is 4-methyl-thiophene-3-carboxaldehyde or 4-(bromo or chloro)-thiophene-3-carboxaldehyde. Precursor thiophenes of type BB, may be produced by much the same method as those of type AA with the use of different starting materials. The method just described to produce precursor thiophenes of type AA may be employed to produce those of type BB where the starting material is not 2-bromo or 5-bromo substituted. Thus, the halogen metal exchange may be employed with 2-(methyl or chloro)-3-bromo-4-(methyl or chloro or bromo) thiophene or 2-(methyl or chloro)-3-bromo-5-(methyl or chloro) thiophene to produce type BB precursor thiophenes which are 2-(methyl or chloro)-4-(methyl or chloro or bromo)-thiophene-3-carboxaldehyde or 2-(methyl or chloro)-5-(methyl or chloro)-thiophene-3-carboxaldehyde. Precursor thiophenes of type CC may be produced from 2-(methyl or chloro or bromo)-4-(methyl or chloro or bromo)-thiophene-3-carboxylate or 2-(methyl or chloro or bromo)-5-(methyl or chloro or bromo)-thiophene-3-carboxylate by two methods. In the first method, the carboxylate starting material is converted to the acid chloride and reacted with N,O-dimethylhydroxylamine to produce the Weinreb amide, thiophene type CC. In the second method, the carboxylate is reacted with N,O-dimethylhydroxylamine and an appropriate coupling agent, such as, DCC or CDI, to produce the Weinreb amide.

The precursor imidazole may be reacted with any of the precursor thiophenes of types AA or BB or CC by use of the Grignard Reaction. Where the precursor thiophene is of type AA or BB, a solution of the thiophene precursor is combined with a solution of the imidazole precursor at room temperature and the reaction is quenched with aqueous ammonium chloride solution to produce an imidazo thienyl methanol.

The carbinol is deoxygenated to final product, where R is hydrogen, by use of a reducing agent, such as borane methyl sulfide in combination with TFA. Alternatively, the methanol is catalytically deoxygenated to final product, where R is hydrogen, by heating with Pearlman's catalyst and an equivalent of acid. To produce final product where R is methyl, the methanol is oxidized to the corresponding ketone with an oxidizing agent, such as $MnO_2$ or Jones Reagent and the resulting ketone is reacted with methyl Grignard to produce a carbinol which is deoxygenated as described immediately above. Where the precursor thiophene is of type CC, a solution of the thiophene precursor is combined with a solution of the imidazole precursor at room temperature and the reaction is quenched with aqueous ammonium chloride solution to produce an imidazo thienyl ketone. To produce final product, the ketone is reduced to the carbinol by use of a reducing agent, such as, sodium borohydride or lithium aluminum hydride and thereafter the carbinol is deoxygenated as described immediately above.

The protecting group on the precursor imidazole is exemplified herein as trityl, which is preferred. However, a person skilled in the art will readily recognize that other protecting groups are suitable. Suitable protecting groups include dimethylsulfamoyl or methoxymethyl. The trityl group is removed in the deoxygenation to final product or upon heating in a dilute acid and alcoholic solvent.

The most preferred compounds of the present invention are shown in Table I:

TABLE I

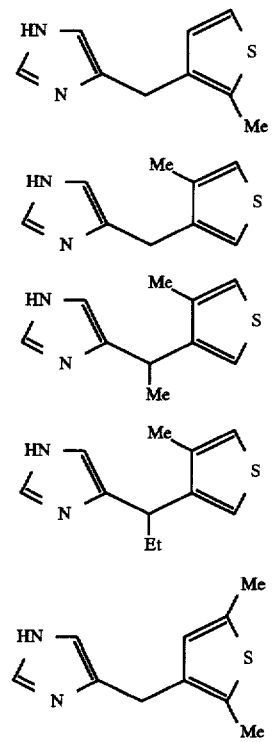

TABLE I-continued

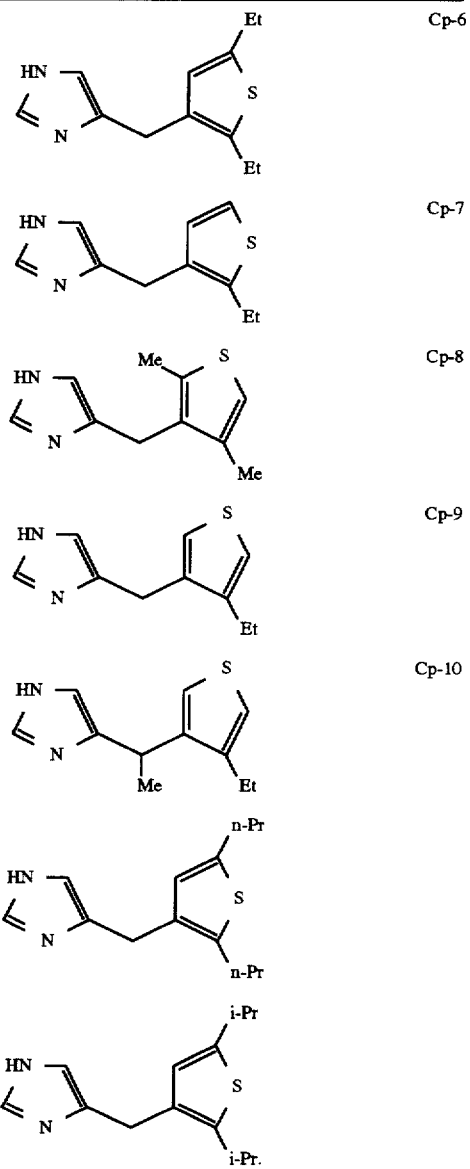

The activity of compounds of the invention as analgesics may be demonstrated by the in vivo and in vitro assays as described below:

Alpha$_{2D}$ adrenergic receptor binding assay

Male, Wistar rats (150–250 g, VAF, Charles River, Kingston, N.Y.) are sacrificed by cervical dislocation and their brains removed and placed immediately in ice cold HEPES buffered sucrose. The cortex is dissected out and homogenized in 20 volumes of HEPES sucrose in a Teflon®-glass homogenizer. The homogenate is centrifuged at 1000 g for 10 min, and the resulting supernatant centrifuged at 42,000 g for 10 min. The resulting pellet is resuspended in 30 volumes of 3 mM potassium phosphate buffer, pH 7.5, preincubated at 25° C. for 30 min and recentrifuged. The resulting pellet is resuspended as described above and used for the receptor binding assay. Incubation is performed in test tubes containing phosphate buffer, 2.5 mM $MgCl_2$, aliquots of the synaptic membrane fraction, the ligand $^3$H-paraaminoclonidine and test drug at 25°0 C. for 20 min. The incubation is terminated by filtration of the tube contents through glass fiber filter sheets. Following washing of the sheets with 10 mM HEPES buffer, the adhering radioactivity is quantified by liquid scintillation spectrometry.

Binding of the test drug to the receptor is determined by comparing the amount of radiolabeled ligand bound in control tubes without drug to the amount of radiolabeled ligand bound in the presence of the drug. Dose-response data are analyzed with LIGAND, a nonlinear curve fitting program designed specifically for the analysis of ligand binding data. This assay is described by Simmons, R. M. A., and Jones, D. J., Binding of [$^3$H-]prazosin and [$^3$H-]p-aminoclonidine to α-Adrenoceptors in Rat Spinal Cord, Brain Research 445:338–349, 1988.

Mouse Acetylcholine Bromide-Induced Abdominal Constriction Assay

The mouse acetylcholine bromide-induced abdominal constriction assay, as described by Collier et al. in *Brit. J. Pharmacol. Chem. Ther.*, 32:295–310, 1968, with minor modifications was used to assess analgesic potency of the compounds herein. The test drugs or appropriate vehicle were administered orally (p.o.) and 30 minutes later the animal received an intraperitoneal (i.p.) injection of 5.5 mg/kg acetylcholine bromide (Matheson, Coleman and Bell, East Rutherford, N.J.). The mice were then placed in groups of three into glass bell jars and observed for a ten minute observation period for the occurrence of an abdominal constriction response (defined as a wave of constriction and elongation passing caudally along the abdominal wall, accompanied by a twisting of the trunk and followed by extension of the hind limbs). The percent inhibition of this response to a nociceptive stimulus (equated to % analgesia) was calculated as follows: The % Inhibition of response, i.e., % analgesia is equal to the difference between the number of control animals response and the number of drug-treated animals response times 100 divided by the number of control animals responding.

At least 15 animals were used for control and in each of the drug treated groups. At least three doses were used to determine each dose response curve and ED$_{50}$ (that dose which would produce 50% analgesia). The ED$_{50}$ values and their 95% fiducial limits were determined by a computer assisted probit analysis.

TABLE II

| Compound | Ki(nm) | Mouse Abdominal Constriction | |
|---|---|---|---|
| | | % Inhibition | ED$_{50}$ |
| Cp-1 | 0.44 | 100% @30 mpk | |
| Cp-2 | 0.47 | | 0.4 mpk |
| Cp-3 | 0.39 | | 0.4 mpk |
| Cp-4 | 0.97 | 100% @30 mpk | |
| Cp-5 | 0.69 | | 1.3 mpk |
| Cp-6 | 0.4 | | 3.7 mpk |
| Cp-7 | 0.07 | | 0.4 mpk |
| Cp-8 | 0.10 | 100% @30 mpk | |
| Cp-9 | 0.29 | 100% @30 mpk | |
| Cp-10 | 0.28 | 100% @30 mpk | |

TABLE II-continued

| Compound | Ki(nm) | Mouse Abdominal Constriction | |
|---|---|---|---|
| | | % Inhibition | ED$_{50}$ |
| (structure) | 6.1 | 100% @30 mpk | |
| (structure) | 3.1 | | 6.4 mpk |
| (structure) | 2.3 | | 1.6 mpk |
| (structure) | 2.5 | 100% @30 mpk | |
| (structure) | 33.5 | | 7.8 mpk |
| (structure) | 11.4 | 67% @30 mpk | |
| (structure) | 1.1 | 100% @30 mpk | |
| (structure) | 0.98 | 27% @30 mpk | |

Based on the above results, invention compounds of the present invention may be used to treat mild to moderately severe pain in warm-blooded animals, such as, humans by administration of an analgesically effective dose. The dosage range would be from about 10 to 3000 mg, in particular about 25 to 1000 mg or about 100 to 500 mg, of active ingredient 1 to 4 times per day for an average (70 kg) human although it is apparent that activity of individual compounds of the invention will vary as will the pain being treated. Pharmaceutical compositions of the invention comprise the formula (I) compounds as defined above, particularly in admixture with a pharmaceutically-acceptable carrier.

To prepare the pharmaceutical compositions of this invention, one or more compounds of the invention or salt thereof as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The pharmaceutically acceptable salts referred to above generally take a form in which the imidazolyl ring is protonated with an inorganic or organic acid. Representative organic or inorganic acids include hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic or saccharic.

The following Examples illustrate the invention:

EXAMPLE 1

4-[(2-Methylthien-3-yl)methyl]-1H-imidazole Fumarate

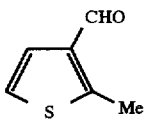

A1

To a solution of 3-bromo-2-methyl thiophene (4.2 g, 24 mmol) in 50 mL of dry Et$_2$O cooled to −78° C. was added n-BuLi (15.0 mL, 24 mmol) dropwise. The bath temperature was allowed to rise to −20° C. and DMF (2.3 mL, 30 mmol) was added. The reaction mixture was allowed to warm to room temperature overnight. The reaction was quenched with NH$_4$Cl (aq) and extracted with Et$_2$O. The organic layer washed twice with water and brine and then dried (MgSO$_4$). After evaporation of solvent, the crude product was purified on flash silica gel (95:5 hexane/Et$_2$O) to afford 2-methylthiophene-3-carboxaldehyde, A1, as a light yellow oil (1.5 g, 50%). $^1$H NMR (CDCl$_3$) supported the assigned structure.

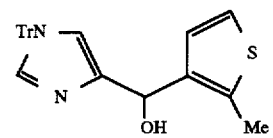

B1

To a solution of N-trityl-4-iodo-imidazole (11.8 g, 27 mmol) in dry CH$_2$Cl$_2$ (75 mL) was added EtMgBr (10.0 mL, 3.0M in Et$_2$O) and the solution was stirred for 3 hrs. Then a solution of 2-methylthiophene-3-carboxaldehyde (3.3 g, 27 mmol) in CH$_2$Cl$_2$ (20 mL) was added and the reaction mixture was stirred at room temperature overnight. The reaction was quenched with NH$_4$Cl (aq) and the mixture was transferred to a separatory funnel. The aqueous layer was extracted with a second portion of CH$_2$Cl$_2$. The extracts were combined and washed with a small portion of water, dried (Na$_2$SO$_4$), and filtered. The solvent was evaporated in vacuo to give a thick syrup which was triturated with Et$_2$O to give a solid which was recrystallized with charcoal treatment from EtOAc to give (2-methylthien-3-yl)-1-trityl-imidazol-4-yl-methanol, B1. $^1$H NMR (CDCl$_3$) supported the assigned structure.

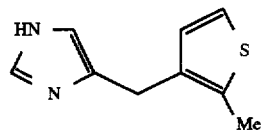

Cp-1

A solution of (2-methylthien-3-yl)-1-trityl-imidazol-4-yl-methanol (1.5 g, 3.5 mmol) was combined with HCl (3.4 mmol) and Pd(OH)$_2$ (1.5 g) in EtOH and hydrogenated (55 psi) at 55° C. for 48 hrs. The catalyst was removed by filtration through Dicalite and the solvent was evaporated in vacuo. The residue was dissolved in water, washed twice with Et$_2$O, and then basified with Na$_2$CO$_3$ and extracted twice with EtOAc. The combined extracts were dried (K$_2$CO$_3$), filtered and solvent evaporated. The residue was chromatographed on flash silica gel (99:0.75:0.25 EtOAc/MeOH/NH$_4$OH) to give a thick syrup which was dissolved in 2-PrOH and combined with fumaric acid (116 mg). The solvent was evaporated and the residue recrystallized from acetone to give the target compound, m.p. 140°–141° C. $^1$H NMR (DMSO-d$_6$) supported the assigned structure: δ 2.3 (s, 3H), 3.75 (s, 2H), 6.6 (s, 2H), 6.75 (s, 1H), 6.85 (d, J=5.3 Hz, 1H), 7.15 (d, 1H), 7.65 (s, 1H). Elemental Analysis: Calc. for C$_9$H$_{10}$N$_2$S.C$_4$H$_4$O$_4$ C, 53.05; H, 4.79; N, 9.52. Found C, 53.22; H, 4.87; N, 9.50.

EXAMPLE 2

4-[(4-Methylthien-3-yl)methyl]-1H-imidazole Fumarate

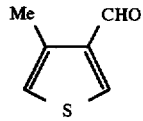

A2

To a solution of 3-bromo-4-methylthiophene (5.3 g, 30 mmol) in 100 mL of dry Et$_2$O cooled to −78° C. was added n-BuLi (20.0 mL, 32 mmol) dropwise. The reaction mixture was allowed to slowly warm to −20° C. and was maintained at this temperature for 30 min. DMF (4.6 mL, 60 mmol) was added and, the reaction mixture was allowed to come to ambient temperature overnight. The reaction was quenched with aqueous ammonium chloride, and the mixture was extracted twice with Et₂O. The organic layers were combined and washed twice with water and then brine and dried (MgSO₄). After filtration, the solvent was evaporated in vacuo. The residue was chromatographed on flash silica gel (98/2 hexane:Et₂O) to give 4-methylthiophene-3-carboxaldehyde, A2, (1.9 g, 50%) as a light yellow oil. ¹H NMR (CDCl₃) supported the assigned structure.

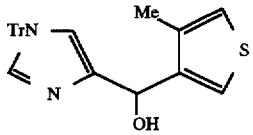

To a solution of N-trityl-4-iodo-imidazole (11.8 g, 27 mmol) in dry CH₂Cl₂ (75 mL) was added EtMgBr (10.0 mL, 3.0M in Et₂O), and the solution was stirred for 3 hrs. Then a solution of 4-methylthiophene-3-carboxaldehyde (3.3 g, 27 mmol) in CH₂Cl₂ (25 mL) was added. The reaction mixture was stirred at room temperature overnight and then was quenched with aqueous NH₄Cl. The mixture was transferred to a separatory funnel, and the aqueous layer was extracted with a second portion of CH₂Cl₂. The combined extracts were washed with a small portion of water, dried (Na₂SO₄), and filtered. The solvent was evaporated in vacuo to give a thick syrup which was triturated with Et₂O to give a solid which was recrystallized with charcoal treatment from EtOAc to give (4-methylthien-3-yl)-1-trityl-imidazol-4-yl-methanol, B2. ¹H NMR (CDCl₃) supported the assigned structure.

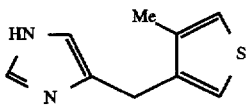

A solution of (4-methylthien-3-yl)-1-trityl-imidazol-4-yl-methanol (2.5 g, 5.7 mmol) was combined with 1N HCl (6 mL) and Pd(OH)₂ (1.25 g) in EtOH and hydrogenated (55 psi) at 50° C. for 48 hrs. The catalyst was removed by filtration through Dicalite, and the solvent was evaporated in vacuo. The residue was dissolved in water, washed twice with Et₂O, and then basified with Na₂CO₃ and extracted twice with EtOAc. The combined extracts were dried (K₂CO₃), filtered, and the solvent was evaporated. The residue was dissolved in 2-PrOH and combined with fumaric acid (0.57 g, 1 eq.). After standing overnight a white solid was collected and recrystallized from acetone to give the title compound m.p. 142°–144° C. ¹H NMR (DMSO-d₆) supported the assigned structure: δ2.15 (s, 3H), 3.75 (s, 2H), 6.6 (s, 2H), 6.75 (s, 1H), 7.05 (m, 1H), 7.15 (m, 1H), 7.65 (s, 1H). Elemental analysis: Calc. for C₉H₁₀N₂S.C₄H₄O₄ C, 53.05; H, 4.79; N, 9.52. Found C, 53.03; H, 4.73; N, 9.38.

EXAMPLE 3

4-[1-(4-Methylthien-3-yl)ethyl]-1H-imidazole Fumarate

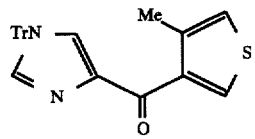

To a solution of (4-methylthien-3-yl)-1-trityl-imidazol-4-yl-methanol, B2, (6.5 g, 14.9 mmol) in 100 mL of CH₂Cl₂ was added MnO₂ (13 g). The mixture was stirred at room temperature for 3 hr and then filtered through Dicalite and the solvent was evaporated in vacuo to give (4-methylthien-3-yl)-1-trityl-imidazol-4-yl-methanone, A3. ¹H NMR (CDCl₃) supported the assigned structure.

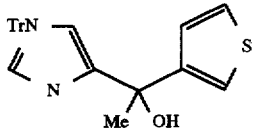

To a solution of (4-methylthien-3-yl)-1-trityl-imidazol-4-yl-methanone, A3, (6.5 g, 14.9 mmol) in 75 mL of THF was added MeMgBr (3.0M in Et₂O) until TLC indicated complete reaction of starting material. The reaction was quenched with aqueous NH₄Cl and extracted twice with EtOAc. The organic extracts were combined, washed with water, then dried (Na₂SO₄) and filtered. The solvent was evaporated in vacuo and the residue was triturated with Et₂O to give 1-[(4-methylthien-3-yl)-1-trityl-imidazol-4-yl]-ethanol, B3. ¹H NMR (CDCl₃) supported the assigned structure.

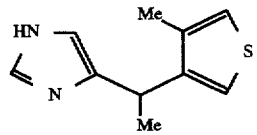

A solution of 1-[(4-methylthien-3-yl)-1-trityl-imidazol-4-yl]-ethanol, B3, (3.1 g, 6.9 mmol), 1N HCl (7.1 mL) and Pd(OH)₂ (1.75 g) in 50 mL of EtOH was hydrogenated (60 psi) at 50° C., for 60 hrs. After cooling, the catalyst was removed by filtration and solvent evaporated in vacuo. The residue was dissolved in water, and was washed twice with Et₂O, then basified with Na₂CO₃ and extracted twice with EtOAc. The organic extracts were combined, dried (K₂CO₃), and filtered. The solvent was evaporated in vacuo and the residue was combined with fumaric acid (0.73 g, 1 eq) in 2-PrOH. A white solid was collected and recrystallized from acetone to give the target compound (1.8 g, 51%) as a white crystalline solid, m.p. 132°–134° C. ¹H NMR (DMSO-d₆) supported the assigned structure. δ1.5 (d, J=7.1 Hz, 3H), 2.1 (s, 3H), 4.05 (q, 1H), 6.6 (s, 2H), 6.65 (s, 1H), 7.1 (s, 2H), 7.65 (s, 1H)

Elemental analysis: Calc. for C₁₀H₁₂N₂S.C₄H₄O₄ C, 54.53; H, 5.23; N, 9.08. Found C, 54.44; H, 5.37; N, 9.00.

EXAMPLE 4

4-[1-(4-Methylthien-3-yl)propyl]-1H-imidazole Fumarate

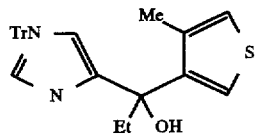

To a solution of (4-methylthien-3-yl)-1-trityl-imidazol-4-yl-methanone, A3, (2.1 g, 4.8 mmol) in 35 mL of THF was added 4.0 mL of EtMgBr (3.0M in Et₂O). The reaction was quenched with aqueous NH₄Cl and extracted twice with Et₂O. The organic extracts were combined, washed with water and brine and then dried (Na₂SO₄) and filtered. The solvent was evaporated in vacuo, and the residue (1-[(4-methylthien-3-yl)-1-trityl-imidazol-4-yl]-propanol), A, was used directly in the next step.

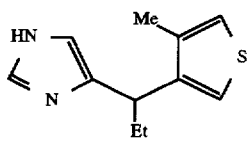

Cp-4

A solution of 1-[(4-methylthien-3-yl)-1-trityl-imidazol-4-yl]-propanol, A4, 1N HCl (5.0 mL) and Pd(OH)$_2$ (1.5 g) in 40 mL of EtOH was hydrogenated (60 psi) at 50° C. overnight. An additional 0.5 g of catalyst was added and hydrogenation was resumed overnight once again. After cooling, the catalyst was removed by filtration and solvent evaporated in vacuo. The residue was dissolved in water, and was washed twice with Et$_2$O, then basified with Na$_2$CO$_3$ and extracted twice with EtOAc. The organic extracts were combined, dried (K$_2$CO$_3$), and filtered. The solvent was evaporated in vacuo, and the residue was chromatographed on flash silica gel (99:0.75:0.25 EtOAc/MeOH/NH$_4$OH) to yield the title compound as a free base (0.38 g, 38% for 2 steps). This was combined with fumaric acid (0.21 g) in 2-PrOH and the solvent was evaporated in vacuo. The residue was recrystallized from acetone to give the target compound (0.30 g) as a white crystalline solid, m.p. 101°–105° C. $^1$H NMR (DMSO-d$_6$) supported the assigned structure. δ0.85 (t, 3H), 1.95 (m, 2H), 2.15 (s, 3H), 3.85 (t, 1H), 6.6 (s, 2H), 6.75 (s, 1H), 7.05 (m, 1H), 7.15 (m, 1H), 7.65 (s, 1H). Elemental analysis: Calc. for C$_{11}$H$_{14}$N$_2$S.C$_4$H$_4$O$_4$ C, 55.89; H, 5.63; N, 8.69. Found C, 55.87; H, 5.69; N, 8.56

EXAMPLE 5

4-[(2,5-dimethylthien-3-yl)methyl]-1H-imidazole Fumarate

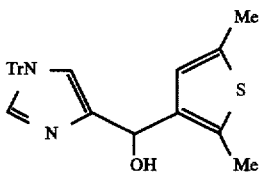

A5

To a solution of N-trityl-4-iodo-imidazole (11.8 g, 27 mmol) in dry CH$_2$Cl$_2$ (200 mL) was added EtMgBr (11.0 mL, 3.0M in Et$_2$O). After complete halogen-metal exchange this solution was cannulated into a solution of 2,5-dimethylthiophene-3-carboxaldehyde (3.5 g, 25 mmol) in 50 mL of CH$_2$Cl$_2$. The reaction mixture was stirred at room temperature for 1 hr and then quenched with aqueous NH$_4$Cl. The mixture was transferred to a separatory funnel and the aqueous layer was extracted with a second portion of CH$_2$Cl$_2$. The combined extracts were dried (MgSO$_4$) and filtered. The solvent was evaporated in vacuo to give a thick syrup which was triturated with Et$_2$O to give a solid which was recrystallized from acetone to give (2,5-dimethylthien-3-yl)-1-trityl-imidazol-4-yl-methanol, A5. $^1$H NMR (CDCl$_3$) supported the assigned structure.

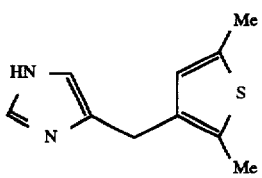

Cp-5

A solution of [(2,5-dimethylthien-3-yl)-1-trityl-imidazol-4-yl]-methanol, A5, (3.4 g, 6.9 mmol), concentrated HCl (0.31 g) and Pd(OH)$_2$ (1.75 g) in 40 mL of 95% EtOH was hydrogenated (60 psi) at 50° C., for 60 hrs. After cooling, the catalyst was removed by filtration and solvent evaporated in vacuo. The residue was dissolved in water, and was washed twice with Et$_2$O, then basified with Na$_2$CO$_3$ and extracted twice with EtOAc. The organic extracts were combined, dried (K$_2$CO$_3$), and filtered. The solvent was evaporated in vacuo and the residue was combined with fumaric acid in 2-PrOH. A white solid was collected and recrystallized from acetone to give the target compound (0.63 g, 27%) as a white crystalline solid m.p. 148°–149° C. $^1$H NMR (DMSO-d$_6$) supported the assigned structure. δ2.37 (s, 3H), 2.39 (s, 3H), 3.65 (s, 2H), 6.6 (s, 2H), 6.7 (s, 1H), 7.65 (s, 1H).

Elemental analysis: Calc. for C$_{10}$H$_{12}$N$_2$S.C$_4$H$_4$O$_4$ C, 54.53; H, 5.23; N, 9.08. Found C, 54.74; H, 5.10; N, 9.00.

EXAMPLE 6

4-[(2,5-diethylthien-3-yl)methyl]-1H-imidazole Fumarate

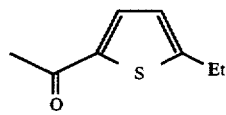

A6

To a mixture of 2-ethylthiophene (56.1 g, 0.5 mol) and acetic anhydride (59 mL) cooled in an ice bath was added 1 mL of HClO$_4$. The reaction mixture became quite dark and there was a vigorous exothermic reaction. After 1 hr, the mixture was diluted with CH$_2$Cl$_2$ and poured onto ice/NaHCO$_3$. This mixture was transferred to a separatory funnel, and the organic layer was washed with an additional portion of dilute NaHCO$_3$, water, dried (MgSO$_4$) and filtered. The solvent was evaporated in vacuo to give a brown oil which was distilled in vacuo (6–8 mm Hg). The product, A6, was collected at 120°–121° C. as a colorless liquid. $^1$H NMR (CDCl$_3$) supported the assigned structure.

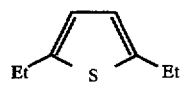

B6

5-Ethyl-2-acetythiophene, A6, (18.5 g, 0.12 mol) was added to hydrazine hydrate (30.0 mL) in 75 mL of ethylene glycol, and the mixture was heated in an oil bath to 170° C. The excess hydrazine and water were distilled out of the reaction mixture. After cooling to room temperature, KOH (24.9 g, 0.44 mol) was added and again the mixture was heated in an oil bath to 120° C., at which point a vigorous reaction and gas evolution began. Heating at 120°–130° C. was continued as the product was distilled from the reaction mixture. The distillate was extracted twice with Et$_2$O. The extracts were then combined and washed with 3N HCl, water and finally brine and then dried (MgSO$_4$) and filtered. The solvent was evaporated in vacuo and the residue was distilled at ambient pressure (175°–177° C.) to give 2,5-diethylthiophene, B6, (10.3 g, 61%) as a colorless liquid. $^1$H NMR (CDCl$_3$) supported the assigned structure.

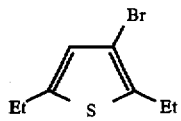

C6

A solution of Br$_2$ (6.4 g, 40.0 mmol) in CHCl$_3$ (25 mL) was added dropwise to a solution of 2,5-diethylthiophene, B6, (5.6 g, 40 mmol) in CHCl₃ (75 mL). The reaction was stirred for 2 hrs at room temperature and then poured onto ice/NaHSO₃. The organic layer was then washed with saturated NaHCO₃, and then water and then dried (MgSO₄) and filtered. The solvent was evaporated in vacuo and the residue was distilled at reduced pressure (1 mm Hg) and 3-bromo-2,5-diethylthiophene, C6, was collected as 5.0 g (57%) of a clear liquid b.p. 79°–81° C. @ 1 mm Hg. ¹H NMR (CDCl₃) supported the assigned structure.

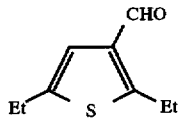   D6

To a solution of 3-bromo-2,5-diethyl thiophene, C6, (9.1 g, 41 mmol) in 100 mL of dry Et₂O cooled to –78° C. was added n-BuLi (26.2 mL, 42 mmol) dropwise. The bath temperature was allowed to rise to –20° C. and DMF (6.3 mL, 82 mmol) was added. The reaction mixture was allowed to warm to room temperature overnight. The reaction was quenched with NH₄Cl (aq) and extracted with Et₂O. The organic layer washed twice with water and brine and then dried (MgSO₄). After evaporation of solvent, the crude product was purified on flash silica gel (98:2 hexane/Et₂O) to afford 2,5-diethylthiophene-3-carboxaldehyde, D6, as a light yellow oil (5.0 g, 72%). ¹H NMR (CDCl₃) supported the assigned structure.

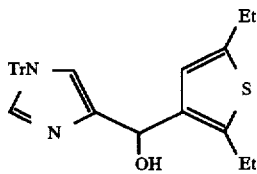   E6

To a solution of N-trityl-4-iodo-imidazole (13.5 g, 31 mmol) in dry CH₂Cl₂ (75 mL) was added EtMgBr (10.0 mL, 3.0M in Et₂O) and the solution was stirred for 3 hrs. Then a solution of 2,5-diethylthiophene-3-carboxaldehyde, D6, (5.0 g, 30 mmol) in CH₂Cl₂ (20 mL) was added, and the reaction mixture was stirred at room temperature overnight. The reaction was quenched with NH₄Cl (aq) and the mixture was transferred to a separatory funnel. The aqueous layer was extracted with a second portion of CH₂Cl₂. The extracts were combined and washed with a small portion of water, dried (Na₂SO₄), and filtered. The solvent was evaporated in vacuo to give a thick syrup which was triturated with Et₂O to give a solid which was recrystallized from EtOAc to give (2,5-diethylthien-3-yl)-1-trityl-imidazol-4-yl-methanol, E6. ¹H NMR (CDCl₃) supported the assigned structure.

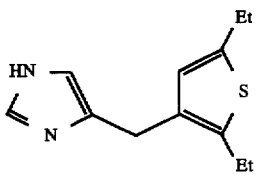   Cp-6

To a solution of TFA (9.2 mL, 120 mmol) in dry CH₂Cl₂ (50 mL) cooled in an ice bath, was added BH₃.Me₂S (90.0 mL, 1.0M in CH₂Cl₂) dropwise. This was stirred at 0° C. for an additional 90 min and then [(2,5-diethylthien-3-yl)-1-trityl-imidazol-4-yl]-methanol, E6, (1.4 g, 3 mmol) in CH₂Cl₂ (25 mL) was added in one portion and reaction mixture was allowed to come to room temperature overnight. The reaction was quenched by the addition of 100 mL of 3:1 MeOH/3N HCl followed by refluxing for 2 hrs. Most of the solvent was then evaporated in vacuo. The residue was dissolved in water and washed twice with Et₂O, then basified with Na₂CO₃ and extracted twice with EtOAc. The organic extracts were combined, dried (K₂CO₃) and filtered. The solvent was evaporated in vacuo to give a syrup (0.69 g), which was combined with fumaric acid (0.36 g) in MeOH. The solvent was evaporated and the residue was recrystallized from acetone to give the title compound (0.70 g, 70%) as a white solid, m.p. 115°–116.5° C. ¹H NMR (DMSO-d₆) supported the assigned structure: 1.2 (m, 6H), 2.7 (m, 4H), 3.7 (s, 2H), 6.55 (s, 1H), 6.6 (s, 2H), 6.75 (s, 1H), 7.6 (s, 1H). Elemental Analysis: Calc for C₁₂H₁₆N₂S.C₄H₄O₄ C, 57.13; H, 5.99; N, 8.33. Found C, 57.06; H, 6.06; N 8.27.

EXAMPLE 7

4-[(2-Ethylthien-3-yl)methyl]-1H-imidazole Fumarate

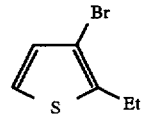   A7

To a mixture of 2-ethylthiophene (11.2 g, 0.100 mol) and sodium acetate (16.4 g, 0.200 mol) in 75 mL of water was added bromine (32.0 g, 0.200 mol). The reaction mixture was stirred for 2 days. GC analysis indicated that some monobrominated material was left so additional bromine (7.75 g) and sodium acetate (5.00 g) were added. After a few hours of stirring, GC analysis indicated that the monobromo material was gone so zinc (19.6 g, 0.30 mol) was added in portions. The reaction mixture was then refluxed for 25 h. The product was distilled out of the reaction mixture. The distillate was extracted with ether twice. The ether extracts were combined, washed with aqueous sodium bicarbonate, water, and brine, and then dried (MgSO₄). The solution was concentrated in vacuo, and then distilled under reduced pressure to provide 10.1 g (53%) of 3-bromo-2-ethylthiophene, A7, b.p. 49°–50° C. @ 4mmHg. The ¹H NMR in CDCl₃ supported the desired product structure.

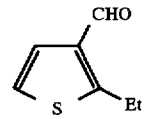   B7

A solution of 3-bromo-2-ethylthiophene, A7, (8.9 g, 0.0465 mol) in 50 mL of diethyl ether was cooled to –78° C., and a solution of n-BuLi (29.0 mL, 1.6M) in hexanes was added dropwise. When the addition was complete, the reaction was stirred at –78° C. for 5 min. Then DMF (5.1 g, 0.070 mol) was cannulated into the reaction mixture which was allowed to warm to ambient temperature and was stirred overnight. The reaction was quenched with water and extracted twice with diethyl ether. The organic extracts were combined, washed with twice with water and then brine and dried (MgSO₄). The solution was filtered and concentrated to provide an oil which was purified on flash silica gel with 97.5:2.5 hexanes:diethyl ether to give 1.66 g (25%) of 2-ethylthiophene-3-carboxaldehyde, B7. The ¹H NMR in CDCl₃ supported the desired product structure.

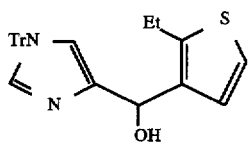

To a solution of N-trityl-4-iodo-imidazole (4.1 g, 0.0095 mol) in dry $CH_2Cl_2$ (75 mL) was added a solution of MeMgBr (4.0 mL, 3.0M) in diethyl ether and the solution was stirred for 3 hrs. Then a solution of 2-ethylthiophene-3-carboxaldehyde, B7, (1.66 g, 0.0087 mol) in $CH_2Cl_2$ (20 mL) was added and the reaction mixture was stirred at room temperature overnight. The reaction was quenched with aqueous $NH_4Cl$ and the mixture was transferred to a separatory funnel. The aqueous layer was extracted with a second portion of $CH_2Cl_2$. The extracts were combined and washed with a small portion of water, dried ($Na_2SO_4$), and filtered. The solvent was evaporated in vacuo, and the residue was triturated with $Et_2O$ to give (2-ethylthien-3-yl)-1-trityl-imidazol-4-yl-methanol, C7, as a beige solid which was taken on to the next step directly.

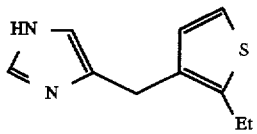

A solution of (2-methylthien-3-yl)-1-trityl-imidazol-4-yl-methanol, C7, (0.9 g, 0.00199 mol) was combined with 1N HCl (2.0 mL) and $Pd(OH)_2$ (1.5 g) in EtOH and hydrogenated (55 psi) at 50° C. for 48 hrs. The catalyst was removed by filtration through Dicalite, and the solvent was evaporated in vacuo. The residue was dissolved in water, washed twice with $Et_2O$, and then basified with $Na_2CO_3$ and extracted twice with EtOAc. The combined extracts were dried ($K_2CO_3$), filtered and solvent evaporated. The residue was dissolved in 2-PrOH and combined with fumaric acid. The solvent was evaporated and the residue recrystallized from acetone to provide 4-[(2-ethylthien-3-yl)methyl]-1H-imidazole fumarate, Cp-7, as a white solid, m.p. 132°–134° C. $^1H$ NMR (DMSO-d6) supported the assigned structure: δ1.20 (t, J=7.5 Hz, 3H), 2.8 (q, J=7.5 Hz, 2H), 3.80 (s, 2H), 6.65 (s, 2H), 6.70 (s, 1H), 6.80 (d, 1H), 7.20 (d, 2H), 7.60 (s, 1H). Elemental Analysis: Calc. for $C_{10}H_{12}N_2S·C_4H_4O_4$ C, 54.33; H, 5.23; N, 9.09. Found C, 54.42; H, 5.17; N, 9.02.

EXAMPLE 8

4-[(2,4-Dimethylthien-3-yl)methyl]-1H-imidazole Fumarate

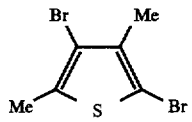

A solution of 2,4,5-tribromo-3-methylthiophene (50.2 g, 0.15 mol; Gronowitz, S.; Moses, P. Hakansson Arkiv. f. Kemi. 1960, 14, 267) in 400 mL of diethyl ether was cooled to -78° C., and a solution of nBuLi (100 mL, 1.6M) was added dropwise. The starting material precipitated out of solution, but when n-BuLi added, the reaction mixture became stirrable again. When the addition was complete, the reaction mixture was stirred for 20 min, and then a solution of dimethyl sulfate (75.7 g, 0.600 mol) in 200 mL of diethyl ether which was cooled to -50° C. was added by cannulation. When addition was complete, the reaction mixture was allowed to warm to ambient temperature and was stirred overnight. The reaction was quenched with 100 mL of 6N NaOH solution and stirred for 2h. The mixture was transferred to a separatory funnel, and the aqueous layer was separated and extracted with additional ether. The organic layers were combined, washed with water and brine and dried ($MgSO_4$). The suspension was filtered and concentrated to give an oil. Vacuum distillation provided 22.1 g (55%) of 2,4-dibromo-3,5-dimethylthiophene, A8, b.p. 71°–72° C. @ 0.4 mmHg. The $^1H$ NMR in $CDCl_3$ supported the assigned structure.

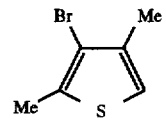

A solution of 2,4-dibromo-3,5-dimethylthiophene, A8, (22.0 g, 0.081 mol) in 250 mL of THF was cooled to -78° C. Then a solution of n-BuLi (53 mL, 1.6M) in hexanes was cooled to -78° C. and added via cannulation. The reaction was stirred for 3 h, and then was quenched with aqueous ammonium chloride. The mixture was extracted twice with diethyl ether. The organic layers were combined, washed with water and brine and dried ($MgSO_4$). The suspension was filtered and concentrated to give an oil. Vacuum distillation provided 7.6 g (49%) of 3-dibromo-2,4-dimethyl thiophene, B8, b.p. 77°–79° C. @ 5 mmHg, as a nearly colorless liquid. The $^1H$ NMR in $CDCl_3$ supported the assigned structure.

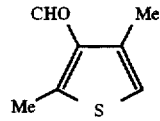

A solution of 3-bromo-2,4-dimethylthiophene, B8, (5.9 g, 0.031 mol) in 200 mL of diethyl ether was cooled to -78° C., and a solution of n-BuLi (25.0 mL, 1.6M) in hexanes was added dropwise. When the addition was complete, the reaction was stirred at -78° C. for 4 h. TLC analysis indicated very little conversion so reaction mixture was warmed slowly to -25° C. Then a solution of DMF (4.5 g, 0.062 mol) in 25 mL of ether was cannulated into the reaction mixture which was allowed to warm to ambient temperature and was stirred overnight. The reaction was quenched with water and extracted twice with diethyl ether. The organic extracts were combined, washed with twice with water and then brine and dried ($MgSO_4$). The solution was filtered and concentrated to provide an amber oil which was dissolved in hexane. The solution was treated with charcoal, filtered through Dicalite, and concentrated to give 2,4-dimethylthiophene-3-carboxaldehyde, C,8, which was used directly in the next step.

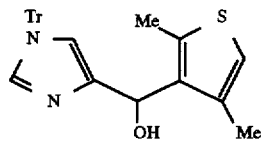

To a solution of 4-iodo-1-trityl imidazole (11.8 g, 0.027 mol) in 75 mL of dry dichloromethane under nitrogen was added dropwise a solution of methyl magnesium bromide in diethyl ether (9.0 mL, 3.0M). When addition was complete, the reaction mixture was stirred for 1 h at 25° C. Then, 2,4-dimethylthiophene-3-carboxaldehyde, C8, (3.8 g, 0.027 mol) was added as a solution in 20 mL of dichloromethane. After overnight stirring at ambient temperature, the reaction was quenched with saturated ammonium chloride solution. The layers were separated, and the aqueous layer was extracted again with dichloromethane. The organic layers were combined, dried (Na$_2$SO$_4$), and concentrated in vacuo. The residue was triturated with ethyl acetate to provide (2,4-dimethylthieno-3-yl)-1-trityl-imidazol-4yl-methanol, D8, as an off-white solid which was taken on directly in the next step.

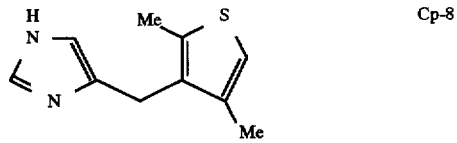

A solution of BH$_3$.Me$_2$S (120 mL, 1.0M) in dichloromethane was added dropwise to a solution of TFA (18.2 g, 0.16 mol) in 50 mL of dry dichloromethane at 0° C. When the addition was complete, the reaction mixture was stirred for 2 h. Then the carbinol, D8, (1.8 g, 0.040 mol) was added, and the reaction mixture was warmed to ambient temperature and stirred overnight. The reaction was quenched with 100 mL of 1.5N HCl, and then the mixture was refluxed on a steam bath for 2 h. The solution was cooled and then concentrated in vacuo to provide a brown oil. The residue was dissolved in water. This solution was washed twice with ether, basified with Na$_2$CO$_3$ and extracted with ethyl acetate. The ethyl acetate extracts were combined, dried (Na$_2$SO$_4$), and concentrated in vacuo. The residue was purified on flash silica gel using 97.5:2.5 chloroform: 10% ammonium hydroxide in methanol. The isolated material was dissolved in isopropanol, and fumaric acid was added. The solvent was removed under reduced pressure, and the residue was recrystallized from acetone to provide 0.274 g of 4-[-(2,4-dimethylthien-3-yl)methyl]-1H-imidazole fumarate, Cp-8, as a white solid, m.p. 160°–162° C. The $^1$H NMR in DMSO-d$_6$ supported the assigned structure: δ2.10 (s, 3H, Me), 2.40 (s, 3H, Me), 3.70 (s, 2H, CH$_2$), 6.55 (s, 1H), 6.65 (s, 2H), 6.85 (s, 1H), 7.60 (s, 1H). Elemental analysis: Calculated for C$_{10}$H$_{12}$N$_2$S.C$_4$H$_4$O$_4$: C, 54.54; H, 5.23; N, 9.08. Found C, 54.45; H, 5.26; N, 9.06.

EXAMPLE 9

4-[(4-Ethylthien-3-yl)methyl]-1H-imidazole Fumarate

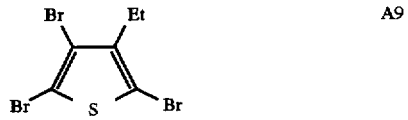

To an ice-cooled solution of 3-ethylthiophene (25.75 g, 0.23 mol) in 75 mL of chloroform was added bromine (111.87 g, 0.7 mol). The reaction mixture was allowed to warm to ambient temperature and was left to stir overnight. Analysis by GC indicated that >90% of a single product was present so the reaction mixture was poured onto ice. The mixture was transferred to a separatory funnel and diluted with additional chloroform. The layers were separated and the organic layer was washed with 200 mL of 10% NaHSO$_3$ solution, water, and brine, and dried (MgSO$_4$). After filtration, concentration in vacuo provided a dark oil which was distilled under reduced pressure to provide 2,3,5-tribromo-4-ethylthiophene, A9. GC analysis indicated that the product was reasonably pure and it was taken on directly.

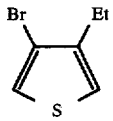

A suspension of zinc (24.5 g, 0.375 mol) in 250 mL of 10% aqueous acetic acid was placed in a round bottom flask fitted with a mechanical stirrer. The suspension was heated at reflux, and 2,3,5-tribromo-4-ethylthiophene, A9, (26.1 g, 0.0750 mol) was added in portions. Reflux was continued overnight, and then the product was removed by steam distillation. The distillate was transferred to a separatory funnel and extracted twice with ether. The ether layers were combined, washed with saturated sodium bicarbonate solution, and dried (MgSO4). After filtration, the solution was concentrated to give 7 g of a clear oil. The original reaction pot was resubjected to steam distillation to provide a second batch of product. Both batches contained a mixture of desired product and dibromo compound. These were purified on flash silica gel with pentane as eluant to provide 3.4 g of 3-bromo-4-ethylthiophene, B9, as a clear liquid. This material was taken on directly in the next step.

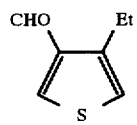

A solution of 3-bromo-4-ethylthiophene, B9, (3.4 g, 0.018 mol) in 40 mL of diethyl ether was cooled to −78° C., and a solution of n-BuLi (12.0 mL, 1.6M) in hexanes was added dropwise. The solution was allowed to warm to −20° C., and DMF (1.46 g, 0.020 mol) was added. The reaction mixture was allowed to warm to ambient temperature and was stirred overnight. The reaction was quenched with aqueous ammonium chloride solution and extracted twice with diethyl ether. The organic extracts were combined, washed with twice with water and then brine and dried (MgSO$_4$). The solution was filtered and concentrated to provide 4-ethylthiophene-3-carboxaldehyde, C9, which was used directly in the next step.

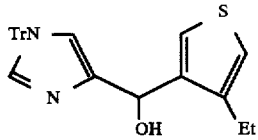

To a solution of 4-iodo-1-trityl imidazole (3.9 g, 0.0090 mol) in 40 mL of dry dichloromethane under nitrogen was added dropwise a solution of ethyl magnesium bromide in diethyl ether (3.0 mL, 3.0M). When addition was complete, the reaction mixture was stirred for 1 h at 25° C. Then, 4-ethyl-thiophene-3-carboxaldehyde, C9, (1.2 g, 0.0086 mol) was added as a solution in 20 mL of dichloromethane. After overnight stirring at ambient temperature, the reaction was quenched with saturated ammonium chloride solution. The layers were separated, and the aqueous layer was extracted again with dichloromethane. The organic layers were combined, dried (Na$_2$SO$_4$), and concentrated to provide an orange-yellow solid. This material was recrystallized from ethyl acetate to provide (4-ethylthiophen-3-yl)1-trityl-imidazo-4-yl-methanol, D9, which was taken on directly in the next step.

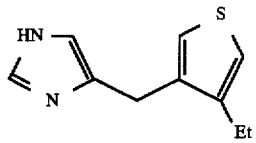
Cp-9

A solution of (4-ethylthien-3-yl)-1-trityl-imidazol-4-yl-methanol, D9, in 40 mL of ethanol containing 1N hydrochloric acid (1.7 mL) and palladium hydroxide (0.75 g) was shaken with hydrogen at 60 psi at 50° C. on a Parr hydrogenator for 3 days. The solution was cooled and filtered to remove the catalyst. The filtrate was concentrated under reduced pressure. The residue was dissolved in water and extracted twice with Et$_2$O then basified with sodium carbonate and extracted with ethyl acetate. The organic layers were combined, dried (K$_2$CO$_3$), and concentrated in vacuo. The residue was dissolved in 2-propanol and fumaric acid was added. The solution was concentrated in vacuo, and the residue was recrystallized from acetone to provide 0.245 g of 4-[(4-ethylthien-3-yl)methyl]-1H-imidazole fumarate, C-9, as a white solid, m.p. 142°–144° C. The $^1$H NMR in DMSO-d$_6$ supported the assigned structure: δ1.20 (t, 3H, Me), 3.8 (s, 2H), 6.65 (s, 2H), 6.67 (s, 1H), 7.05 (m, 1H), 7.10 (m, 1H), 7.60 (s, 1H), 7.55 (s, 1H). Elemental analysis: Calculated for C$_{10}$H$_{12}$N$_2$S.C$_4$H$_4$O$_4$: C, 54.53; H, 5.23; N, 9.08. Found C, 54.58; H, 5.33; N, 9.03.

EXAMPLE 10

4-[(4-Ethylthien-3-yl)ethyl]-1H-imidazole Fumarate

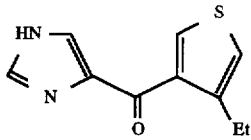
A10

To a solution of the carbinol, D9, (1.17 g, 2.6 mmol) in 50 mL of dichloromethane was added MnO$_2$ (5.0 g). The reaction mixture was stirred overnight and then was filtered. The filtrate was concentrated in vacuo to provide 4-(4-ethylthien-3yl)-1-trityl-imidazol-4yl methanone, A10, which was used directly in the next step.

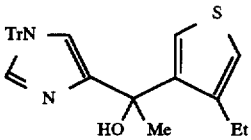
B10

A solution of methylmagnesium bromide (1.0 mL, 3.0M) in diethyl ether was added to an ice-cooled solution of 4-(4-ethylthien-3-yl)-1-trityl-imidazol-4yl methanone, A10, (1.17 g, 0.0026 mol) in 25 mL of THF. After 30 min of stirring, TLC analysis indicated that some starting material was left so an additional 1.0 mL of methylmagnesium bromide was added, and the reaction mixture was stirred over the weekend. The reaction was quenched with aqueous ammonium chloride solution, and the resulting mixture was extracted twice with ethyl acetate. The ethyl acetate extracts were combined, washed with water and brine, dried (Na$_2$SO$_4$), and filtered. Concentration provided 1-(4-ethylthien-3-yl)-1-trityl-imidazol-4-yl ethanol, B10, as an oil which crystallized on standing. This material was taken on directly in the next step.

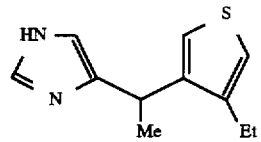
Cp-10

A solution of 1-[(4-ethylthien-3-yl)-1-trityl-imidaz-4-yl]-ethanol, B10, in 40 mL of ethanol containing 1N hydrochloric acid (2.5 mL) and palladium hydroxide (1.0 g) was shaken with hydrogen at 60 psi at 50° C. on a Parr hydrogenator for 3 days. The solution was cooled and filtered to remove the catalyst. The filtrate was concentrated under reduced pressure. The residue was dissolved in water and extracted twice with Et$_2$O, then basified with sodium carbonate and extracted with ethyl acetate. The organic layers were combined, dried (K$_2$CO$_3$), and concentrated in vacuo. The residue was purified on a silica gel column on a Foxy apparatus using 99:0.75:0.25 ethyl acetate:methanol:ammonium hydroxide as eluant to provide a glass. This material was dissolved in 2-propanol and fumaric acid was added. The solution was concentrated in vacuo, and the residue was recrystallized from acetone to provide 0.323 g of 4-[1-(4-ethylthien-3-yl)ethyl]-1H-imidazole fumarate, Cp-10, as a white solid, m.p. 145°–147° C. The $^1$H NMR in DMSO-d$_6$ supported the assigned structure: δ1.50 (t, 3H, Me), 1.50 (d, 2H, Me), 4.05 (q, 1H, CH), 6.60 (s, 3H), 7.05 (d, 1H), 7.15 (d, 1H), 7.55 (s, 1H). Elemental analysis: Calculated for C$_{11}$H$_{14}$N$_2$S.C$_4$H$_4$O$_4$: C, 55.89; H, 5.63; N, 8.69. Found C, 55.79; H, 5.47; N, 8.59.

What is claimed is:

1. A compound of the formulae:

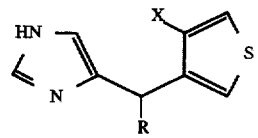

wherein

R is hydrogen or methyl, and

X is C$_{1-4}$alkyl, bromine or chlorine.

2. The compound of claim 1 selected from the group consisting of:

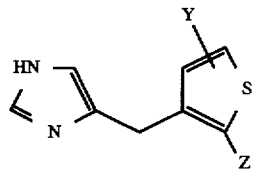

3. A compound of the formulae:

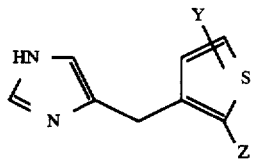

wherein

Y is hydrogen, C$_{1-4}$alkyl, bromine or chlorine, and

Z is C$_{1-4}$alkyl, bromine or chlorine.

4. The compound of claim 3 selected from the group consisting of:

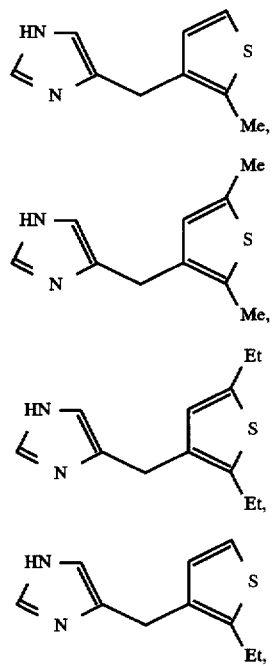
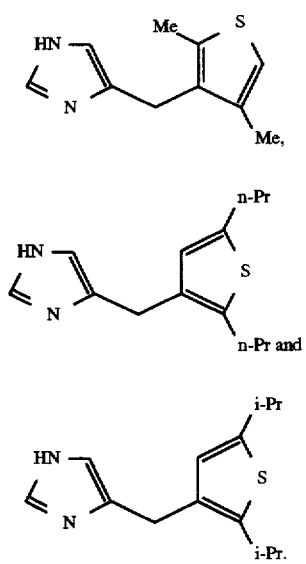
* * * * *

UNITED STATES PATENT AND TRADEMARK OFFICE
CERTIFICATE OF CORRECTION

PATENT NO.    : 5,750,720             Page 1 of 1
DATED         : May 12, 1998
INVENTOR(S)   : Robert E. Boyd, Chris Royce Rasmussen, Jeffrey Press It is certified that error appears in the above-identified patent and that said Letters Patent is hereby corrected as shown below:

Claim 2,
Line 45, please delete "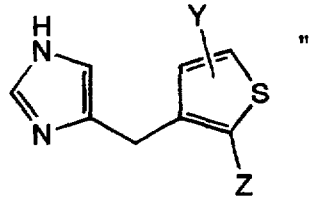"

and insert

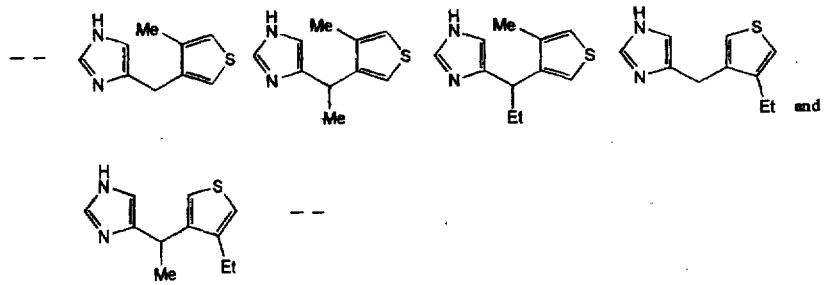

Signed and Sealed this

Fifth Day of March, 2002

*Attest:*

*Attesting Officer*

JAMES E. ROGAN
*Director of the United States Patent and Trademark Office*